United States Patent [19]

Buret et al.

[11] Patent Number: 5,753,622
[45] Date of Patent: May 19, 1998

[54] USE OF EPIDERMAL GROWTH FACTOR AS A GASTROINTESTINAL THERAPEUTIC AGENT

[75] Inventors: Andre G. Buret; D. Grant Gall; James A. Hardin; Merle E. Olson, all of Calgary,, Canada

[73] Assignee: University Technologies International, Inc., Calgary, Canada

[21] Appl. No.: 438,901

[22] Filed: May 10, 1995

[51] Int. Cl.$^6$ .................... C07K 14/485; A61K 38/18
[52] U.S. Cl. ........................................... 514/12; 530/399
[58] Field of Search ........................ 514/2, 12; 530/399

[56] References Cited

FOREIGN PATENT DOCUMENTS 0 161 817   11/1985   European Pat. Off. .
2 198 351    6/1988   United Kingdom .

OTHER PUBLICATIONS

Zadunaisky et al. J. Membrane Biol. 143:207–217, 1995.
Karasovz et al. Physiol. Gastrointes. Tract. 2nd Ed. Johnson, Raven & Press, New York, pp. 1489–1497, 1987.
Newsted et al. Toxicol. Appl. Pharmacol. 119:41–51, 1993.
Johnson et al. Mol. Cell. Biol. 8(5):1970–1978, 1988.
"Textbook of Endocrinology", 5th Ed. Edited by R.H. Williams, W.B. Saunders Co. 1974.
Barrett. Gastroenterology 104(1):326–327, 1994.
Donnenberg. Gastroenterology 107:1193–1196, 1994.
Zijlstra et al. J. Ped. Gastroenterol. Nut. 19:382–390, 1994.
Zapata—Sirvent et al. Surgery 113(5):564–573, 1993.
Imada, O. et al., "Long-Latency Growth-Promoting Activity of EGF when Administered to Mice at the Neonatal Stage", Biological Abstracts, vol. 84 No. 12 Abstract No. 117708 (1987).
Lyall, R. M. et al., "Tyrphostins Inhibit Epidermal Growth Factor (EGF) –Receptor Tyrosine Kinase Activity in Living Cells and EGF-Stimulated Cell Proliferation", Journal of Biological Chemistry, vol. 264 No. 24 pp. 14503–14509 (1989).
Zschiesche, W. et al., "Effects of Anti-EGF Serum on Newborn Mice", Experientia, vol. 44 No. 3 pp. 249–251 (1988).
Bird, A.R. et al. (1994) "Jejunal Glucose Absorption is Enhanced by Epidermal Growth Factor in Mice" J. Nutr. 124:231–240.
Brown, G.L. et al. (1986) "Enhancement of Epidermal Regeneration by Biosynthetic Epidermal Growth Factor" J. Exp. Med. 163:1319–1324.
Goodlad, R.A. et al. (1991) "Effects of Urogastrone–Epidermal Growth Factor on Intestinal Brush Border Enzymes and Mitotic Activity" Gut. 994–998.
Hardin, J.A. et al. (1993) "Effect of Epidermal Growth Factor on Enterocyte Brush–Border Surface Area" Am. J. Physiol. 264:G312–G318.
Hardin, J.A. et al. (1992) "The Effect of TGFα on Intestinal Solute Transport" Reg. Pep. 39:169–176.
Horvath, K. et al. (1994) "Short–Term Effect of Epidermal Growth Factor on Sodium and Glucose Cotransport of Isolated Jejunal Epithelial Cells" Biochem. Biophys. Acta Mol. Cell. Res. 1222: 215–222.
Kitagawa, T. et al. (1989) "Regulations of Glucose Transport Activity and Expression of Glucose Transporter mRNA by Serum, Growth Factors, and Phorbol Ester in Quiescent Mouse Fibroblasts"Biochem. Biophys. Acta. 980:100–108.
O'Loughlin, E.V. et al. (1985) "Effect of Epidermal Growth Factor on Ontogeny of the Gastrointestinal Tract" Am. J. Physiol. 249:G674–G678.
O'Loughlin, E.V. et al. (1994) "Structural and Functional Adaptation Following JeJunal Resection in Rabbits: Effect of Epidermal Growth Factor" Gastroenterology 107:87–93.
Opleta–Madsen, K. (1991) "Epidermal Growth Factor Upregulates Intestinal Electrolyte and Nutrient Transport" Am. J. Physiol. 260:G807–G814.
Opleta–Madsen, K. (1991) "Epidermal Growth Factor and Postnatal Development of Intestinal Transport and Membrane Structure" Pediatr. Res. 30:342–350.
Pothier, P. et al. (1988) "Presence and Characteristics of Epidermal Growth Factor Receptors in Human Fetal Small Intestine and Colon" FEBS Lett. 228(1):113–117.
Walker–Smith, J.A. et al. (1985) "Intravenous Epidermal Growth Factor/Urogastrone Increases Small Intestinal Cell Proliferation in Congenital Microvillous Atrophy" Lancet ii:1239–1240.
Weaver, L.T. et al. (1990) "Uptake and Transport of Epidermal Growth Factor by the Small Intestinal Epithelium of the Fetal Rat" Gastroenterology 98:828–837.
Zijlstra, R.T. et al. (1994) "Effect of Orally Administered Epidermal Growth Factor in Intestinal Recovery of Neonatal Pigs Infected with Rotavirus" J. Ped. Gastro. Nutr. 19:382–390.
Bliska, J.B. et al. (1993) "Signal Transduction in the Mammalian Cell During Bacterial Attachment and Entry" Cell. 73:903–920.
Brown, G.L., et al. (1989) Enhancement of Wound Healing by Topical Treatment with Epidermal Growth Factor New Engl. J. Med. 321(2):76–79.

(List continued on next page.)

Primary Examiner—John Ulm
Assistant Examiner—Christine Saoud
Attorney, Agent, or Firm—Bereskin & Parr; Micheline Gravelle

[57] ABSTRACT

A method of inhibiting or treating gastrointestinal colonization of a pathogen in an animal by administration of epidermal growth factor is described. A method of increasing weight gain in an animal by administrating epidermal growth factor is also described. The epidermal growth factor can be administered orally for example in the feed or drinking water of the animal. Since EGF is useful in inhibiting or treating intestinal colonization by a pathogen and is also effective in promoting weight gain, EGF is useful in treating a wide range of intestinal infections. In one embodiment, a method of treating or inhibiting enteric colibacillosis using epidermal growth factor is described.

6 Claims, 1 Drawing Sheet

OTHER PUBLICATIONS

Buchmiller, T.L. et al. (1993) "Effect of Transamniotic Administration of Epidermal Growth Factor on Fetal Rabbit Small Intestinal Transport and Disaccharidase Development" *J. Ped. Surg. 28(10)*:1239–1244.

Carpenter, G. (1993) "EGF: New Tricks for an Old Growth Factor" *Curr. Opinion Cell Biol. 5*:261–264.

Donowitz, M. et al. (1994) "Brush Border Tyrosine Phosphorylation Stimulates Ileal Neutral NaCl Absorption and Brush Border $Na^+H^+$ Exchange" *Am. J. Physiol. 266*:G647–G656.

Eppstein, D.A. et al. (1985) "Epidermal Growth Factor Receptor Occupancy Inhibits Vaccinia Virus Infection" *Nature 318*:663–665.

Foltzer–Jourdainne C. et al. (1993) "Epidermal Growth Factor and the Maturation of Intestinal Sucrase in Suckling Rats" *Am. J. Physiol. 265(28)*:G459–G466.

Galan, J.E. et al. (1992) "Involvement of the Epidermal Growth Factor Receptor in the Invasion of Cultured Mammalian Cells by Salmonella Typhimurium" *Nature 357*:588–589.

Isberg, R.R. (1991) "Discrimination Between Intracellular Uptake and Surface Adhesion of Bacterial Pathogens" *Sciencel 252*:934–938.

Jaeger, L.A. et al. (1990) "Effect of Orally Administered Epidermal Growth Factor on the Jejunal Mucosa of Weaned Pigs" *Am. J. Vet. Res. 5(3)*:471–474.

James, P.S. et al. (1987) "Dexamethasone Selectively Increases Sodium–Dependent Alanine Transport Across Neonatal Piglet Intestine" *J. Physiol. 393*:569–582.

James, P.S. et al. (1987) "Epidermal Growth Factor Selectively Increases Maltase and Sucrase Activities in Neonatal Piglet Intestine" *J. Physiol. 393*:583–594.

Komoriya, A. et al. (1984) "Biologically Active Synthetic Fragments of Epidermal Growth Factor: Localization of a Major Receptor–Binding Region" *Proc. Natl. Acad. Sci. USA 81*:1351–1355.

Marti, U. et al. (1989) "Biological Effects of Epidermal Growth Factor with Emphasis on the Gastrointestinal Tract and Liver: An Update" *Hepatology 9(1)*:126–138.

Opleta, K. et al. (1987) "Effect of Epidermal Growth Factor on Growth and Postnatal Development of the Rabbit Liver" *Am. J. Physiol. 253(16)*:G622–G626.

Pace, J. et al. (1993) "Signal Transduction and Invasion of Epithelial Cells by Salmonella Typhimurium" *Cell. 72*:505–514.

Pascall, J.C. et al. (1991) "Cloning and Characterization of a Gene Encoding Pig Epidermal Growth Factor" *J. Mol. Endocrinol. 6*:63–70.

Salloum, R.M. et al. (1993) "Regulation of Small Intestinal Glutamine Transport By Epidermal Growth Factor" *Surgery 113*:552–559.

Smith, M.W. (1988) "Postnatal Development of Transport Function in the Pig Intestine" *Comp. Biochem. Physiol. 90A*:577–582.

Strong, J.E. et al. (1993) "Evidence that Epidermal Growth Factor Receptor on Host Cells Confers Reovirus Infection Efficiency" *Virology 197*:405–411.

Tang, D. et al. (1993) "Recognition of the Epidermal Growth Factor Receptor by Reovirus" *Virology 197*:412–414.

Barnard, J.A. et al. (1995) "Epidermal Growth Factor–Related Peptides and Their Relevance to Gastrointestinal Pathophysiology" *Gastroenterology 108*:564–580.

Playford, R.J. et al. (1993) "Effect of Luminal Growth Factor Preservation of Intestinal Growth" *Lancet 341*:843–848.

Schwartz, M.Z. et al. (1988) "Influence of Epidermal Growth Factor on Intestinal Function in the Rat: Comparison of Systemic Infusion Versus Luminal Perfusion" *Am. J. Surg. 155*:18–22.

CURVE FITS: —— Control: $Y = -3.2222 + 43.1800 X$ ($R = 0.9985$)

--- EGF: $Y = -9.2806 + 48.3117 X$ ($R = 0.9997$)

USE OF EPIDERMAL GROWTH FACTOR AS A GASTROINTESTINAL THERAPEUTIC AGENT

FIELD OF THE INVENTION

This invention relates to a method of promoting weight gain and preventing gastrointestinal colonization by pathogens by oral administration of epidermal growth factor. EGF may be used to increase absorption of warranted substances, or, conversely inhibition of the EGF signalling cascade may be used to prevent uptake of toxic or adverse compounds as well as to promote weight loss. In one embodiment, the invention relates to the treatment of enteric colibacillosis by oral administration of epidermal growth factor.

BACKGROUND OF THE INVENTION

A number of intestinal growth factors accelerate epithelial maturation and renewal. One of these, epidermal growth factor (EGF) is naturally present in salivary and intestinal secretions and other body fluids, and is produced in large guantities in colostrum and milk. EGF promotes a) the proliferation and differentiation of intestinal cells during early life, b) the functional maturation of the pre-weaning intestine, and c) epithelial proliferation in the adult gut (10,11,12,13,14). Moreover, EGF acutely (within minutes) upregulates small intestinal absorption of electrolytes and nutrients, an effect which was shown to be related to a concurrent lengthening of the apical microvilli of enterocytes (15). Potential therapeutic benefits of EGF have been highlighted in studies where topical treatment with EGF promoted wound healing (30) and, more recently, by the observation that administration of EGF enhances nutrient absorption in remnant intestine following massive resection (16). Compared with the small intestine, more receptors for EGF are found in the colon (17), where the heaviest bacterial load is observed during infection with microorganisms such as *Esherichia coli*. EGF upregulates function in the entire intestine, including the colon (12, 16).

While EGF has been reported to have a variety of functions, its role in preventing intestinal colonization by pathogens or in accelerating weight gain have not been previously reported. These two newly discovered properties of EGF make it extremely useful as a therapeutic agent in young farm animals as EGF can prevent intestinal infection in the animals and at the same time cause an increase in rate of weight gain in the animals. Many pathogens are known to infect and cause death in young animals. In order to demonstrate the utility of EGF in preventing intestinal colonization the inventors have chosen enteric colibacillosis as a model system.

Enteric colibacillosis is a bacterial infection with considerable implications for the agricultural economy. Enteric colibacillosis (also called scours) is one of the most common diseases of newborn and young farm animals (1). The microbe responsible for the disease is the pathogenic bacterium *Escherichia coli* (*E. coli*). The infection occurs wherever farm animals are maintained and is a significant cause of economic loss in Western Canada and other parts of the world. The disease is characterized by diarrhea, dehydration and eventual death. Overcrowding of young animals in confined areas is commonly followed by outbreaks of enteric colibacillosis. Dairy calves receiving milk replacer are more susceptible to enteric colibacillosis than those fed cow's milk, and when they are raised under intensified conditions, the rate of morbidity due to infection with *E. coli* may reach 75% (1,2,3). In pigs, enteric colibacillosis is responsible for about half of all intestinal diseases seen during the preweaning period and is also an important cause of death in weanling piglets (1,4,5,6).

Partly because of the great variability of antigens found in the *E. coli* microorganisms responsible for the disease, the development of a scours-vaccine has proven extremely challenging. Therefore, there is a real need to develop a method to prevent the economic loss caused by enteric colibacillosis.

Enteric colibacillosis is caused mainly by two types of *E. coli* microorganisms: 1) Entero-toxigenic *E. coli* and 2) Attaching and effacing *E. coli*. Both types of bacteria enter the host by being ingested. The microbe then adheres to enterocytes of the gut wall, initially in the small intestine, and multiplies to form microcolonies. From there, *E. coli* colonizes the distal parts of the intestine, thus amplifying the disease process. Clearly, initial colonization plays an essential role in the pathogenesis of enteric colibacillosis (4,7,8). It was recently demonstrated that host as well as bacterial factors were a major cause of the diarrhea during infection with toxin-producing *E. coli* (9). Indeed, when neutrophils, the principal bacteria-killing cell, were not allowed to accumulate in the infected mucosa, electrolyte secretion and malabsorption (and diarrhea) were suppressed despite the presence of the bacteria. This observation challenges the long-accepted view of a direct causal relationship between toxins released by *E. coli* and the production of diarrhea. These and other studies give rise to novel opportunities for the clinical management of enteric colibacillosis, and, as protective vaccination has proven difficult to achieve, modulating the intestinal surface of the host appears particularly appealing. Also noteworthy is the fact that more than 80% of disease cases caused by *E. coli* occur in calves younger than 4 days of age (2,3). The mechanisms of this obvious age-dependent resistance are not fully understood. Possible explanations include maturation of the enterocytes or absorption of maternal immunoglobulins from colostrum, milk, or other sources. The potential clinical benefits of accelerating the maturation and/or replacement of enterocytes or the stimulation of increased immunoglobulin absorption in the context of intestinal infection have never been explored.

In view of the above, there is a need to develop a method for preventing colonization by pathogens in the intestine of young farm animals. Intestinal infection and disease is the major cause of loss in food producing animals. The present inventors have shown the oral administration of EGF can prevent intestinal colonization by pathogens. The inventors have also shown that EGF can enhance weight gain in animals. The latter effect is unexpected as certain publications have indicated that EGF has no effect on weight gain (21,25). Other studies investigating the effects of EGF in pigs (28,29) were unable to demonstrate an acceleration in growth rate, despite concurrent increases in the levels of intestinal disaccharidases.

In addition to preventing colonization by pathogens and to increasing weight gain, the administration of EGF to young farm animals may also have other potential benefits. For example, due to its role in the upregulation of gastrointestinal absorption, EGF may similarly affect immunoglobulin uptake in the newborn.

The major source of immunoglobins for the newborn is maternal colostrum and milk, and failure to appropriately absorb maternal immunoglobins correlates with high morbidity and mortality from infectious diseases (31). The rate of immunoglobulin absorption is greatest during the first days of life, after which immunoglobulin uptake decreases and gut closure occurs. Administration of EGF may (a) promote immunoglobulin absorption from colostrum, milk or other sources (such as oral immunoglobulin preparations) and (b) delay gut closure which may also enhance immunoglobulin uptake.

As discussed above, EGF causes an increase in the intestinal absorption of nutrients. On the other hand, inhibition of the EGF signalling cascade reduces intestinal absorption of nutrients. However, the clinical benefits of inhibiting of EGF signalling cascade in the regulation of gastrointestinal nutrient absorption have never been assessed. It is predicted that antagonists of the EGF receptor or the EGF signalling cascade may be used as gastrointestinal therapeutic agent where decreased intestinal absorption may be warranted for example in treating obesity, or to decrease intestinal uptake of toxic or adverse substances.

SUMMARY OF THE INVENTION

The present invention relates to the use of epidermal growth factor (EGF) as a gastrointestinal therapeutic agent. In the agricultural industry, particularly in the beef, pig and poultry industry, there is a demand for non-drug food additives that may enhance production. Intestinal infection and disease is the major cause of loss in food producing animals. One of these infections, enteric colibacillosis (scours) is a very common and devastating disease in young farm animals.

In one aspect, the present invention provides a method for preventing intestinal colonization by pathogens in an animal which comprises administering EGF to said animal. The EGF is preferably administered orally, for example in the feed of the animal. Further, lyophilized EGF added to drinking water has proven stable and therefore can be administered as such.

In a preferred embodiment, the present invention provides a method of treating enteric colibacillosis (scours) by oral administration of EGF. However, since the mechanism of action of EGF is not specific, EGF may also prevent the colonization of other bacteria or other pathogens such as viruses and parasites.

In another aspect, the present invention provides a method of increasing weight gain in an animal which comprises administering EGF to said animal.

In a further aspect, the present invention provides a method of increasing immunoglobulin absorption in a newborn animal which comprises administering EGF to said animal.

In yet a further aspect, the present invention provides a method of decreasing intestinal absorption of nutrients which comprises administering an agent that inhibits the activity of EGF to said animal. Such a method may be useful in situations where decreased intestinal absorption is desired such as in treating obesity or in decreasing the intestinal absorption of toxins.

DESCRIPTION OF THE DRAWINGS

The FIGURE is a graph showing the effect of EGF on weight gain in rabbits.

DETAILED DESCRIPTION OF THE INVENTION

Example 1

Figure 1:
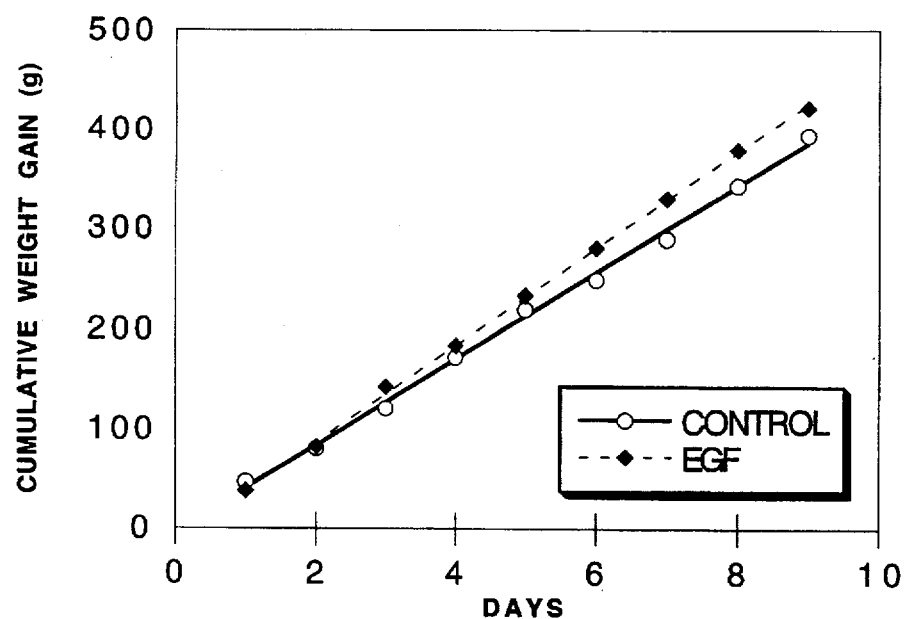

Effects of EGF on intestinal infection.

A preliminary study using 15 New Zealand white rabbits (6 week old, 500–700 g) was carried out to test the hypothesis that EGF may protect from intestinal colonization with *E. coli*. Animals were divided in three groups: 1) unmanipulated controls, 2) animals orally infected with *E. coli*, and 3) animals orally infected with *E. coli* and given daily oral dosages of 60 µg recombinant human EGF (Austral Biologicals, San Ramon, Calif. 94583) for 10 days starting 3 days prior to infection. All animals were checked daily for weight gain, food intake, rectal passage of *E. coli*, and presence of diarrhea. Results are summarized in the table 1. Clinically, in untreated infected animals, rectal swabs were positive for *E. coli* 2 days after inoculation and 3 out of 5 rabbits showed signs of diarrhea by day 7. In contrast, infected animals given daily doses of 60 µg EGF excreted *E. coli* a day earlier and did not show signs of diarrhea. Controls had no diarrhea or *E. coli* (either from rectal swabs or in the intestines at necropsy). Compared to controls, 7 days after infection, infected animals had a reduced cumulative weight gain, poorer feed conversion efficiency, and decreased mucosal wet weights in the ileum and proximal colon. EGF treatment reduced bacterial colonization in the proximal colon by 62%, protected mucosal weight in ileum and colon, and improved feed conversion efficiency and weight gain (Table 1). Feed efficiency and weight gain in treated-infected animals were comparable to noninfected controls.

Example 2

Effects of EGF on weight gain:

EGF was tested for its potential benefits on weight gain. One group of New Zealand white rabbits (6 week old, 500–700 g) received daily oral doses of recombinant human EGF (100 µg/kg body weight) and control animals were given saline only. At 9 days, EGF-treated animals had a mean cumulative weight gain of 422+27 g (n=10) while controls only gained 394 +16 g (n=11). Referring to the FIGURE, the slope of the linear regression curve of weight gain in EGF treated animals was significantly greater (P 0.002) than that of untreated controls. Given the linear aspect of both curves, continued feeding with EGF is likely to produce a steadily increasing effect on weight gain. Examples 1 and 2 indicate that EGF as a food additive and as a gastrointestinal therapeutic agent may 1) promote the acceleration of weight gain in healthy animals and 2) provide significant clinical benefits in the management of intestinal infection (bacterial, viral and possibly others).

Example 3

Inhibition of EGF to decrease weight gain.

Based on the hypothesis that down regulation of specific components of the EGF signalling cascade may inhibit nutrient absorption, the effects of tyrophostin 51 (Sigma), (a tyrosine-kinase inhibitor), on nutrient absorption and brush border ultrastructure were tested. Tyrophostin 51 is a specific inhibitor of tyrosine kinase, which is a critical element of the EGF signalling cascade. Two experimental 10 cm jejunal loops separated by a 1 cm blind loop were tied off in New Zealand White rabbits (8 week old, 700–1000 g). Tyrophostin (10 µM in 1.5 mL of saline) was injected into one experimental loop. The other loop received vehicle alone as a control. After one hour, brush border membrane vesicles were prepared from both loops and assessed for nutrient (D-glucose) absorption. In addition, using transmission electron microscopy, the height of brush border microvilli was measured. The height of the brush border microvilli is a parameter that has been established as the limiting factor for overall brush border surface area in the inventor's previous studies. The preliminary findings demonstrate that treatment with tyrophostin 51 decreases nutrient uptake (26.9±2.8 nmol/min/mg Prot) and microvillus height (1.05±0.20 µm) when compared to control values (transport=36.6±1.8 nmol/min/mg Prot; microvillus height= 1.90±0.15 µm). The inventor's have previously demonstrated that levels of intestinal nutrient absorption and diffuse microvillus membrane surface area correlate with weight gain in a number of different models. Thus, it is predicted that treatment with tyrophostin may promote decreased weight gain or weight loss and therefore may be useful in the treatment of obesity. As well, such treatment may be used to reduce the intestinal uptake of toxic or adverse substances.

The above describes new utilites for EGF. In particular, EGF has been shown to prevent gastrointestinal colonization by pathogens and to promote weight gain in animals. Further, EGF may increase immunoglobulin absorption in young animals. Consequently, EGF is a very useful agent that can be used to increase production in the animal industry such as the beef, pig and poultry industry. In addition, EGF treatment may have clinical benefits in humans (i.e. during Crohn's disease, gastrointestinal infection, traveller's diarrhea, etc.)

Inhibitors of EGF may decrease nutrient absorption in the intestine and as such may be useful in treating obesity or in preventing absorption of toxins.

One skilled in the art will appreciate that the present invention relates to new utilities of EGF and inhibitors of EGF. The examples described are meant to be models to exemplify the invention and not to limit the invention. The mode of administration, the formulation and the dose of the EGF or EGF Inhibitor can be varied depending on the particular utility. For example, when treating young farm animals the EGF can be administered orally in the feed or drinking water of the animal. The dose range can be varied from 10–10,000 µg/kg per day.

TABLE 1

|  | Cumulative Weight Gain[1] | Feed Efficiency[2] | Mucosal Wet Weight[3] | | E. Coli[4] |
|---|---|---|---|---|---|
|  |  |  | ileum | prox. colon |  |
| CONTROL | 358 ± 15 | 2.2 ± 0.2 | 122 ± 5 | 198 ± 15 | — |
| INFECTED | 293 ± 33 | 3.3 ± 1.3 | 116 ± 6 | 170 ± 11 | 4.41 ± 0.23 |
| INFECTED + EGF | 335 ± 24 | 1.8 ± 0.3 | 128 ± 6 | 195 ± 17 | 3.99 ± 0.24 [62%] |

Values are means ± Standard error from mean of 5 animals per group 7 days after inoculation, [%] percent bacterial clearance
[1] grams
[2] Food intake/weight gain
[3] milligram/cm
[4] Log 10 CFU (per cm prox colon)

REFERENCES

1. Radostits O M, Blood D C, Gay C C (eds). Veterinary medicine. Baillere Tindall 8th Ed., London. 1994, pp 703–730.
2. Acres S D. Enterotoxigenic E. coli infections in newborn calves: a review. J. Dairy Sci. 1985:68;229–256.
3. Janke B H, Francis D H, Collins J E, et al. Attaching and effacing E. coli infection as a cause of diarrhea in young calves. JAVMA 1990;196(6) :897–901.
4. Grimes S D, Waxler G L, Newman J P. Adhesion of K99-positive E. coli to intestinal brush borders of pigs. Am J Vet Res. 1986;47(2) :385–388.
5. Bijlsma IGW, deNijs A, van der Meer C, et al. Different pig phenotypes affect adherence of E. coli to jejunal brush borders by K88ab, K88ac, K88ad antigen. Infect Immun 1982;37:891–894.
6. Mainil J G, Bex F, Jacguemin E, et al. Prevalence of four enterotoxin (STaP,STaH,STb,and LT) and four adhesin subunit (K99,K88.987P, and F41) genes among E. coli isolates from cattle. Am J Vet Res. 1990;51(2) 187–190.
7. Schoonderwoerd M, Clarke R C, van Dreumal A A, et al. Colitis in calves: Natural and experimental infection with a verotoxin-producing strain of E. coli 0111:NM. Can J Vet Res. 1988;52:484–487.
8. Hadad J J, Gyles C L. Scanning and transmission electron microscopic study of the small intestine of colostrum-fed calves infected with selected strains of E. coli. Am J Vet Res. 1982;43(1) 41–49.
9. Elliott E, Li Z, Bell C, et al. Modulation of host response to E. coli 0157:H7 infection by antiCD18 antibody in rabbits. Gastroenterology 1994;106:1554–1561.
10. Weaver L T; Gonella P A, Israel E J, et al. Uptake and transport of Epidermal Growth Factor by the small intestinal epithelium of the fetal rat. Gastroenterology 1990;98:828–837.
11. O'Loughlin E V, Chung M, Hollenberg M, et al. Effect of epidermal growth factor on ontogeny of the gastrointestinal tract. Am J Physiol 1985;249:G674–G678.
12. Goodlad R A, Raja K B, Peters T J, et al. Effects of urogastrone-epidermal growth factor on intestinal brush border enzymes and mitotic activity. Gut 1991;994–998.
13. Walker-Smith J A, Phillips A D, Walford N, et al. Intravenous epidermal growth factor/urogastrone increases small intestinal cell proliferation in congenital microvillous atrophy. Lancet 1985;ii:1239–1240.
14. Hardin J A, Buret A, Meddings J B, et al. Effect of epidermal growth factor on enterocyte brush-border surface area. Am J Physiol 1993;264:G3120G318.
15. O'Loughlin E V, Winter M, Shun A, et al. Structural and functional adaptation following jejunal resection in rabbits: Effect of epidermal growth factor. Gastroenterology 1994;107:87–93.
16. Pothier P, Menard D. Presence and characteristics of epidermal growth factor receptors in human fetal small intestine and colon. FEBS lett. 1988;228(1) 113–117.
17. Brake A J, Merryweather J P, Coit D G, et al. α-factor directed synthesis and secretion of mature foreign proteins in Saccharomyces cerevisiae. Proc Natl Acad Sci USA 1984;81:4642–4646.
18. Brown G L, Curtsinger L, Brightwell J R, et al. Enhancement of epidermal regeneration by biosynthetic epidermal growth factor. J Exp Med 1986;163:1319–1324.
19. Brown G L, Nanney L B, Griffen J, et al. Enhancement of wound healing by topical treatment with epidermal growth factor. New Engl J Med 1989;321:76–79.
20. Zijlstra R T, Odle J, Hall W F, et al. Effect of orally administred epidermal growth factor in intestinal recovery of neonatal pigs infected with rotavirus. J Ped Gastro Nutr 1994;19:382–390.
21. Bird A R, Croom W J, Fan Y K, et al. Jejunal glucose absorption is enhanced by epidermal growth factor in mice. J Nutr 1994;124:231–240.
22. Hardin J A, Gall D G. The effect of TGFα on intestinal solute transport. Reg Pep 1992;39:169–176.
23. Horwath K, Hill I D, Devarajan P, et al. Short-term effect of epidermal growth factor on sodium and glucose cotransport of isolated jejunal epithelial cells. Biochem Biophys Acta Mol Cell Res 1994;1222:215–222.
24. Kitagawa T, Tanaka M, Akamatsu Y. Regulation of glucose transport activity and expression of glucose transporter mRNA by serum, growth factors, and phorbol ester in quiescent mouse fibroblasts. Biochem Biophys Acta 1989;980:100–108.
25. Opleta-Madsen K, Hardin J A, Gall D G. Epidermal growth factor upregulates intestinal electrolyte and nutrient transport. Am J Physiol 1991;260:G807–G814.
26. Opleta-Madsen K, Meddings J B, Gall D G. Epidermal growth factor and postnatal development of intestinal transport and membrane structure. Pediatr Res 1991;30:342–350.
27. Salloum R M, Stevens B R, Schultz G S, et al. Regulation of small intestinal glutamine transport by epidermal growth factor. Surgery 1993;113:552–559.
28. James P S, Smith M W, Tivey D R, et al. Dexamethasone selectively increases sodium-dependent alanine transport across neonatal piglet intestine. J Physiol 1987;393:569–582.
29. Jaeger L A, Lamar C H, Cline T R, et al. Effect of orally administered epidermal growth factor on the jejunal mucosa of weaned pigs. Am. J. Vet. Res. 1990;5(3):471–474.
30. Brown G L, Nanney L B, Griffin J, et al. Enhancement of wound healing by topical treatment with epidermal growth factor. New Engl. J. Med. 1989;321(2):76–79.
31. Aldridge B, Garry F, Adams R. Role of colostral tranfer in neonatal calf management: Failure of acquisition of passive immunity. Continuing education article #8. Compend. N. Am. Ed. 1992;14(2):265–269.
32. Donowitz M, Montgomery J L M, Walker M S, et al. Brush border tyrosine phosphorylation stimulates ileal neutral NaCl absorption and brush border $Na^+H^+$ exchange. Am J Physiol 1994;266:G647–G656.

What we claim as our invention:

1. A method of inhibiting or treating intestinal colonization of a pathogen in an animal which comprises administrating epidermal growth factor to said animal in need thereof.

2. The method according to claim 1 wherein said epidermal growth factor is administered in the feed of said animal.

3. The method according to claim 1 wherein said epidermal growth factor is administered orally.

4. A method of treating or inhibiting enteric colibacillosis in an animal which comprises administering epidermal growth factor to said animal in need thereof.

5. The method according to claim 4 wherein said epidermal growth factor is administered in the feed of said animal.

6. The method according to claim 4 wherein said epidermal growth factor is administered orally.

* * * * *